(12) United States Patent
Uhr

(10) Patent No.: US 7,667,108 B1
(45) Date of Patent: Feb. 23, 2010

(54) INBRED CORN LINE G07-NPFA7278

(75) Inventor: David Uhr, Evansville, IN (US)

(73) Assignee: Syngenta Participations AG, Basel (CH)

( * ) Notice: Subject to any disclaimer, the term of this patent is extended or adjusted under 35 U.S.C. 154(b) by 165 days.

(21) Appl. No.: 11/713,372

(22) Filed: Mar. 1, 2007

(51) Int. Cl.
 *A01H 5/10* (2006.01)
 *A01H 5/00* (2006.01)
 *A01H 1/00* (2006.01)
 *C12N 5/04* (2006.01)

(52) U.S. Cl. ............. 800/320.1; 800/275; 800/298

(58) Field of Classification Search .............. None
 See application file for complete search history.

(56) References Cited

OTHER PUBLICATIONS

PVP 8300148 issued Feb. 22, 1985 Filing data only.
PVP 8200064 issued May 26, 1983 Filing data only.
PVP 8800152 issued Nov. 30, 1988 Filing data only.

*Primary Examiner*—Ashwin Mehta
(74) *Attorney, Agent, or Firm*—Dana Rewoldt

(57) ABSTRACT

Basically, this invention provides for an inbred corn line designated G07-NPFA7278, methods for producing a corn plant by crossing plants of the inbred line G07-NPFA7278 with plants of another corn plants. The invention relates to the various parts of inbred G07-NPFA7278 including culturable cells. This invention also relates to methods for introducing transgenic transgenes into inbred corn line G07-NPFA7278 and plants produced by said methods.

19 Claims, No Drawings

INBRED CORN LINE G07-NPFA7278

FIELD OF THE INVENTION

This invention is in the field of corn breeding, specifically relating to an inbred corn line designated G07-NPFA7278. This invention also is in the field of hybrid maize production employing the present inbred.

BACKGROUND OF THE INVENTION

The original maize plant was indigenous to the Western Hemisphere. The plants were weed like and only through the efforts of early breeders were cultivated crop species developed. The crop cultivated by early breeders, like the crop today, could be wind pollinated. The physical traits of maize are such that wind pollination results in self-pollination or cross-pollination between plants. Each maize plant has a separate male and female flower that contributes to pollination, the tassel and ear, respectively. Natural pollination occurs when wind transfers pollen from tassel to the silks on the corn ears. This type of pollination has contributed to the wide variation of maize varieties present in the Western Hemisphere.

The development of a planned breeding program for maize only occurred in the last century. A large part of the development of the maize product into a profitable agricultural crop was due to the work done by land grant colleges. Originally, maize was an open pollinated variety having heterogeneous genotypes. The maize farmer selected uniform ears from the yield of these genotypes and preserved them for planting the next season. The result was a field of maize plants that were segregating for a variety of traits. This type of maize selection led to; at most, incremental increases in seed yield.

Large increases in seed yield were due to the work done by land grant colleges that resulted in the development of numerous hybrid corn varieties in planned breeding programs. Hybrids were developed from inbreds which were developed by selecting corn lines and selfing these lines for several generations to develop homozygous pure inbred lines. One selected inbred line was emasculated and another selected inbred line pollinated the emasculated inbred to produce hybrid seed F1 on the emasculated inbred line. Emasculation of the inbred usually is done by detasseling the seed parent; however, emasculation can be done in a number of ways. For example an inbred could have a male sterility factor which would eliminate the need to detassel the inbred.

In the early seventies the hybrid corn industry attempted to introduce CMS (cytoplasmic male sterility) into a number of inbred lines. Unfortunately, the CMS inbreds also introduced some very poor agronomic performance traits into the hybrid seed which caused farmers concern causing the maize industry to shy away from CMS material for a couple of decades thereafter.

However, in the last 10-15 years a number of different male sterility systems for maize have been successfully deployed. The most traditionally of these male sterility and/or CMS systems for maize parallel the CMS type systems that have been routinely used in hybrid production in sunflower.

In the standard CMS system there are three different maize lines required to make the hybrid. First, there is a cytoplasmic male-sterile line usually carrying the CMS or some other form of male sterility. This line will be the seed producing parent line. Second, there must be a fertile inbred line that is the same or isogenic with the seed producing inbred parent but lacking the trait of male sterility. This is a maintainer line needed to make new inbred seed of the seed producing male sterile parent. Third there is a different inbred which is fertile, has normal cytoplasm and carries a fertility restoring gene. This line is called the restorer line in the CMS system. The CMS cytoplasm is inherited from the maternal parent (or the seed producing plant); therefore for the hybrid seed produced on such plant to be fertile the pollen used to fertilize this plant must carry the restorer gene. The positive aspect of this is that it allows hybrid seed to be produced without the need for detasseling the seed parent. However, this system does require breeding of all three types of lines: 1) male sterile—to carry the CMS: 2) the maintainer line; and, 3) the line carrying the fertility restorer gene.

In some instances, sterile hybrids are produced and the pollen necessary for the formation of grain on these hybrids is supplied by interplanting of fertile inbreds in the field with the sterile hybrids.

Whether the seed producing plant is emasculated due to detasseling or CMS or transgenes, the seed produced by crossing two inbreds in this manner is hybrid seed. This hybrid seed is F1 hybrid seed. The grain produced by a plant grown from a F1 hybrid seed is referred to as F2 or grain. Although, all F1 seed and plants, produced by this hybrid seed production system using the same two inbreds should be substantially the same, all F2 grain produced from the F1 plant will be segregating maize material.

The hybrid seed production produces hybrid seed which is heterozygous. The heterozygosis results in hybrid plants, which are robust and vigorous plants. Inbreds on the other hand are mostly homozygous. This homozygosity renders the inbred lines less vigorous. Inbred seed can be difficult to produce since the inbreeding process in corn lines decreases the vigor. However, when two inbred lines are crossed, the hybrid plant evidences greatly increased vigor and seed yield compared to open pollinated, segregating maize plants. An important consequence of the homozygosity and the homogeneity of the inbred maize lines is that all hybrid seed produced from any cross of two such elite lines will be the same hybrid seed and make the same hybrid plant. Thus the use of inbreds makes hybrid seed which can be reproduced readily.

The ultimate objective of the commercial maize seed companies is to produce high yielding, agronomically sound plants that perform well in certain regions or areas of the Corn Belt. To produce these types of hybrids, the companies must develop inbreds, which carry needed traits into the hybrid combination. Hybrids are not often uniformly adapted for the entire Corn Belt, but most often are specifically adapted for regions of the Corn Belt. Northern regions of the Corn Belt require shorter season hybrids than do southern regions of the Corn Belt. Hybrids that grow well in Colorado and Nebraska soils may not flourish in richer Illinois and Iowa soils. Thus, a variety of major agronomic traits is important in hybrid combination for the various Corn Belt regions, and has an impact on hybrid performance.

Inbred line development and hybrid testing have been emphasized in the past half-century in commercial maize production as a means to increase hybrid performance. Inbred development is usually done by pedigree selection. Pedigree selection can be selection in an $F_2$ population produced from a planned cross of two genotypes (often elite inbred lines), or selection of progeny of synthetic varieties, open pollinated, composite, or backcrossed populations. This type of selection is effective for highly inheritable traits, but other traits, for example, yield requires replicated test crosses at a variety of stages for accurate selection.

Maize breeders select for a variety of traits in inbreds that impact hybrid performance along with selecting for acceptable parental traits. Such traits include: yield potential in hybrid combination; dry down; maturity; grain moisture at harvest; greensnap; resistance to root lodging; resistance to stalk lodging; grain quality; disease and insect resistance; ear and plant height. Additionally, Hybrid performance will differ in different soil types such as low levels of organic matter, clay, sand, black, high pH, low pH; or in different environments such as wet environments, drought environments, and no tillage conditions. These traits appear to be governed by a complex genetic system that makes selection and breeding of an inbred line extremely difficult. Even if an inbred in hybrid combination has excellent yield (a desired characteristic), it may not be useful because it fails to have acceptable parental traits such as seed yield, seed size, pollen production, good silks, plant height, etc.

To illustrate the difficulty of breeding and developing inbred lines, the following example is given. Two inbreds compared for similarity of 29 traits differed significantly for 18 traits between the two lines. If 18 simply inherited single gene traits were polymorphic with gene frequencies of 0.5 in the parental lines, and assuming independent segregation (as would essentially be the case if each trait resided on a different chromosome arm), then the specific combination of these traits as embodied in an inbred would only be expected to become fixed at a rate of one in 262,144 possible homozygous genetic combinations. Selection of the specific inbred combination is also influenced by the specific selection environment on many of these 18 traits which makes the probability of obtaining this one inbred even more remote. In addition, most traits in the corn genome are regrettably not single dominant genes but are multi-genetic with additive gene action not dominant gene action. Thus, the general procedure of producing a non segregating $F_1$ generation and self pollinating to produce a $F_2$ generation that segregates for traits and selecting progeny with the visual traits desired does not easily lead to a useful inbred. Great care and breeder expertise must be used in selection of breeding material to continue to increase yield and the agronomics of inbreds and resultant commercial hybrids.

Certain regions of the Corn Belt have specific difficulties that other regions may not have. Thus the hybrids developed from the inbreds have to have traits that overcome or at least minimize these regional growing problems. Examples of these problems include in the eastern corn belt Gray Leaf Spot, in the north cool temperatures during seedling emergence, in the Nebraska region CLN (corn Lethal necrosis and in the west soil that has excessively high pH levels. The industry often targets inbreds that address these issues specifically forming niche products. However, the aim of most large seed producers is to provide a number of traits to each inbred so that the corresponding hybrid can useful in broader regions of the Corn Belt. The new biotechnology techniques such as Microsatellites, RFLPS, RAPDs and the like have provided breeders with additional tools to accomplish these goals.

SUMMARY OF THE INVENTION

The present invention relates to an inbred corn line G07-NPFA7278. Specifically, this invention relates to plants and seeds of this line. Additionally, this relates to a method of producing from this inbred, hybrid seed corn and hybrid plants with seeds from such hybrid seed. More particularly, this invention relates to the unique combination of traits that combine in corn line G07-NPFA7278.

Generally then, broadly the present invention includes an inbred corn seed designated G07-NPFA7278. This seed produces a corn plant.

The invention also includes the tissue culture of regenerable cells of G07-NPFA7278 wherein the cells of the tissue culture regenerates plants capable of expressing the genotype of G07-NPFA7278. The tissue culture is selected from the group consisting of leaf, pollen, embryo, root, root tip, guard cell, ovule, seed, anther, silk, flower, kernel, ear, cob, husk and stalk, cell and protoplast thereof. The corn plant regenerated from G07-NPFA7278 or any part thereof is included in the present invention. The present invention includes regenerated corn plants that are capable of expressing G07-NPFA7278's genotype, phenotype or mutants or variants thereof.

The invention extends to hybrid seed produced by planting, in pollinating proximity which includes using preserved maize pollen as explained in U.S. Pat. No. 5,596,838 to Greaves, seeds of corn inbred lines G07-NPFA7278 and another inbred line if preserved pollen is not used; cultivating corn plants resulting from said planting; preventing pollen production by the plants of one of the inbred lines if two are employed; allowing cross pollination to occur between said inbred lines; and harvesting seeds produced on plants of the selected inbred. The hybrid seed produced by hybrid combination of plants of inbred corn seed designated G07-NPFA7278 and plants of another inbred line are apart of the present invention. This inventions scope covers hybrid plants and the plant parts including the grain and pollen grown from this hybrid seed.

The invention further includes a method of hybrid F1 production. A first generation (F1) hybrid corn plant produced by the process of planting seeds of corn inbred line G07-NPFA7278; cultivating corn plants resulting from said planting; permitting pollen from another inbred line to cross pollinate inbred line G07-NPFA7278; harvesting seeds produced on plants of the inbred; and growing a harvested seed are part of the method of this invention.

The present invention also encompasses a method of introducing at least one targeted trait into maize inbred line comprising the steps of: (A) crossing plant grown from the present invention seed which is the recurrent parent, representative seed of which has been deposited, with the donor plant of another maize line that comprises at least one target trait selected from the group consisting of male sterility, herbicide resistance, insect resistance, disease resistance, amylose starch, and waxy starch to produce F1 plants; (b) selecting from the F1 plants that have at least one of the targeted trait, forming a pool of progeny plants with the targeted trait; (c) crossing the pool of progeny plants with the present invention which is the recurrent parent to produce backcrossed progeny plants with the targeted trait; (d) selecting for backcrossed progeny plants that have at least one of the target trait and physiological and morphological characteristics of maize inbred line of the recurrent parent, listed in Table 1 forming a pool of selected backcrossed progeny plants; and (e) crossing the selected backcrossed progeny plants to the recurrent parent and selecting from the resulting plants for the targeted trait and physiological and morphological characteristics of maize inbred line of the recurrent parent, listed in Table 1 and reselecting from the pool of resulting plants and repeating the crossing to the recurrent parent and selecting step in succession to form a plant that comprise the desired trait and all of the physiological and morphological characteristics of maize inbred line of the recurrent parent if the present invention listed in Table 1 as determined at the 5% significance level when grown in the same environmental conditions.

This method and the following method of introducing traits can be done with less back crossing events if the trait and/or the genotype of the present invention are selected for or identified through the use of markers. SSR, microsatellites, SNP and the like decrease the amount of breeding time required to locate a line with the desired trait or traits and the characteristics of the present invention. Backcrossing in two or even three traits (for example the glyphosate, Europe corn borer, corn rootworm resistant genes) is routinely done with the use of marker assisted breeding techniques. This introduction of transgenes or mutations into a maize line is often called single gene conversion. Although, presently more than one gene particularly transgenes or mutations which are readily tracked with markers can be moved during the same "single gene conversion" process, resulting in a line with the addition of more targeted traits than just the one, but still having the characteristics of the present invention plus those characteristics added by the targeted traits.

The method of introducing a desired trait into maize inbred line comprising: (a) crossing plant grown from the present invention seed, representative seed of which has been deposited the recurrent parent, with plant of another maize line that comprises at least one target trait selected from the group consisting of nucleic acid encoding an enzyme selected from the group consisting of phytase, stearyl-ACP desaturase, fructosyltransferase, levansucrase, amylase, invertase and starch branching enzyme, the donor parent to produce F1 plants; (b) selecting for the targeted trait from the F1 plants, forming a pool of progeny plants; (c) crossing the progeny plants with the recurrent parent to produce backcrossed progeny plants; (d) selecting for backcrossed progeny plants that have at least one of the target trait and physiological and morphological characteristics of maize inbred line of the present invention a listed in Table 1 forming a pool of backcrossed progeny plants; and repeating a step of crossing the new pool with the recurrent parent and selecting for the targeted trait and the recurrent parents characteristics until the selected plant is essentially the recurrent parent with the targeted trait or targeted traits. This selection and crossing may take at least 4 backcrosses if marker assisted breeding is not employed.

The inbred line and seed of the present invention are employed to carry the agronomic package into the hybrid. Additionally, the inbred line is often carrying transgenes that are introduced in to the hybrid seed.

Likewise included is a first generation (F1) hybrid corn plant produced by the process of planting seeds of corn inbred line G07-NPFA7278; cultivating corn plants resulting from said planting; permitting pollen from inbred line G07-NPFA7278 to cross pollinate another inbred line; harvesting seeds produced on plants of the inbred; and growing a plant from such a harvested seed.

A number of different techniques exist which are designed to avoid detasseling in maize hybrid production. Some examples are switchable male sterility, lethal genes in the pollen or anther, inducible male sterility, male sterility genes with chemical restorers. There are numerous patented means of improving upon the hybrid production system. Some examples include U.S. Pat. No. 6,025,546, which relates to the use of tapetum-specific promoters and the barnase gene to produce male sterility; U.S. Pat. No. 6,627,799 relates to modifying stamen cells to provide male sterility. Therefore, one aspect of the current invention concerns the present invention comprising one or more gene(s) capable of restoring male fertility to male-sterile maize inbreds or hybrids and/or genes or traits to produce male sterility in maize inbreds or hybrids.

The inbred corn line G07-NPFA7278 and at least one transgenic gene adapted to give G07-NPFA7278 additional and/or altered phenotypic traits are within the scope of the invention. Such transgenes are usually associated with regulatory elements (promoters, enhancers, terminators and the like). Presently, transgenes provide the invention with traits such as insect resistance, herbicide resistance, disease resistance increased or deceased starch or sugars or oils, increased or decreased life cycle or other altered trait.

The present invention includes inbred corn line G07-NPFA7278 and at least one transgenic gene adapted to give G07-NPFA7278 modified starch traits. Furthermore this invention includes the inbred corn line G07-NPFA7278 and at least one mutant gene adapted to give modified starch, acid or oil traits, i.e. amylase, waxy, amylose extender or amylose. The present invention includes the inbred corn line G07-NPFA7278 and at least one transgenic gene: bacillus thuringiensis, the bar or pat gene encoding Phosphinothricin acetyl Transferase, Gdha gene, GOX, VIP, EPSP synthase gene, low phytic acid producing gene, and zein. The inbred corn line G07-NPFA7278 and at least one transgenic gene useful as a selectable marker or a screenable marker is covered by the present invention.

A tissue culture of the regenerable cells of hybrid plants produced with use of G07-NPFA7278 genetic material is covered by this invention. A tissue culture of the regenerable cells of the corn plant produced by the method described above is also included.

DEFINITIONS

In the description and examples, which follow, a number of terms are used. In order to provide a clear and consistent understanding of the specifications and claims, including the scope to be given such terms, the following definitions are provided.

Early Season Trait Codes

Emergence (EMRGR): rated when 50% of the plots in the trial are at V1 (1 leaf collar) growth stage.

1=All plants have emerged and are uniform in size

3=All plants have emerged but are not completely uniform

5=Most plants have emerged with some just beginning to break the soil surface, noticeable lack of uniformity 7=Less than 50% of the plants have emerged, and lack of uniformity is very noticeable 9=A few plants have emerged but most remain under the soil surface.

Seedling Growth (SVGRR): rated between V3 and V5 (3-5 leaf stage) giving greatest weight to seedling plant size and secondary weight to uniform growth.

1=Large plant size and uniform growth

3=Acceptable plant size and uniform growth

5=Acceptable plant size and might be a little non-uniform

7=Weak looking plants and non-uniform growth

9=Small plants with poor uniformity

Purpling (PRPLR): Emergence and/or early growth rating. Purpling is more pronounced on the under sides of leaf blades especially on midribs.

1=No plants showing purple color

3=30% plants showing purple color

5=50% plants showing purple color

7=70% plants showing purple color

9=90+% plants showing purple color

Herbicide Injury (HRBDR) The herbicide used is listed then rate each hybrid/variety injury as indicated below. The NORTH CENTRAL PUBLICATION # 337, is used as a general reference, it refers to the herbicide mode of action and injury symptoms.

1=No apparent reduction in biomass or other injury symptoms

5=Moderate reduction in biomass with some signs of sensitivity

9=Severe reduction in biomass with some mortality

Mid-Season Traits Codes

Heat Units to 50% Silk (HU5SN): Rated when 50% of all plants within a plot show 2 cm or more silk protruding from the ear. Days are converted to accumulated heat units from planting.

Heat units to 50% Pollen Shed (HUPSN): Rated when 50% of all plants within a plot are shedding pollen. Days are converted to accumulated heat units from planting.

Plant Height in cm (ERHTN): After pollination average plant height of each plot is recorded. Measurement is from ground to base of leaf node.

Plant Ear Height in cm (PLHTN): After pollination average ear height of each plot is recorded. Measurement is from ground to base of ear node (shank).

Root Lodging Early % (ERTLP): Early root lodging occurs up to about two weeks after flowering and usually involves goosenecking. The number of root lodged plants are counted and converted to a percentage. For plots, lodged plants out of 50 plants from two locations in each hybrid strip, are recorded, summed, and a percentage is recorded.

Foliar Disease (LFDSR): Foliar disease ratings should be done one month before harvest through harvest. The predominant disease is listed in the trial information and individual hybrid ratings are given.

1=No lesions to two lesions per leaf.

3=A few scattered lesions on the leaf. About five to ten percent of the leaf surface is affected.

5=A moderate number of lesions are on the leaf. About 15 to 20 percent of the leaf surface is affected.

7=Abundant lesions are on the leaf. About 30 to 40 percent of the leaf surface is affected.

9=Highly abundant lesions (>50 percent) on the leaf. Lesions are highly coalesced. Plants may be prematurely killed.

Data collection (as described above) should focus on the following diseases:

Common Rust (CR) Eye Spot (ES)
Gray Leaf Spot (GLS) Northern Corn Leaf Blight (NCLB)
Stewart's Bacterial Wilt (SBW) Southern Corn Leaf Blight (SCLB)
Southern Rust (SR) Corn Virus Complex (CVC)

Preharvest Trait Codes

Heat units to Black Layer (HUBLN): Rated when 50% of all plants within a plot reach black layer stage. Days are converted to accumulated heat units from planting. Ratings are taken on border rows of four-row plots.

Harvest Population (HAVPN): Count the number of plants in yield rows, excluding tillers, in each plot. For plots, count a thousandth of an acre two times and record the average.

Barren Plants (BRRNP): Count the number of plants in yield rows having no ears and/or abnormal ears with less than 50 kernels. For plots, count barren plants out of 50 from two locations in each hybrid strip, sum, and record the percentage. Data is collected on entire trial.

Dropped Ears (DROPP): Count the numbers of ears lying on the ground in yield rows. For plots, count dropped ears from the area of 50 plants from two locations in each hybrid strip, sum, and the percentage is recorded.

Stalk Lodging % (STKLP): Stalk lodging will be reported as number of plants broken below the ear without pushing, excluding green snapped plants. Only trials with approximately five percent or more average stalk lodging are recorded. Count the number of broken plants in yield rows and convert to percent. For plots, count stalk lodged plants out of 50 from two locations in each hybrid strip, sum, and the percentage is recorded.

Root Lodging Late % (LRTLP): Late root lodging can usually start to occur about two weeks after flowering and involves lodging at the base of the plant. Plants leaning at a 30-degree angle or more from the vertical are considered lodged. Count the number of root lodged plants in yield rows and convert to percent. For plots, count root lodged plants out of 50 from two locations in each hybrid strip, sum, and the percentage is recorded.

Push Test for Stalk and Root Quality on Erect Plants % (PSTSN): The push test is applied to trials with approximately five percent or less average stalk lodging. Plants are pushed that are not root lodged or broken prior to the push test. Standing next to the plant, the hand is placed at the top ear and pushed to arm's length. Push one of the border rows (four-row small plot) into an adjacent plot border row. Count the number of plants leaning at a 30-degree angle or more from the vertical, including plants with broken stalks prior to pushing, do not count plants that have strong rinds that snap rather than bend over easily. For plots, push 50 plants from two interior locations of each hybrid strip, sum, and record the percentage. The goal of the push test is to identify stalk rot and stalk lodging potential, NOT ECB injury. If ECB injury is present, a push test is done on the ECB trials.

Intactness (INTLR):

1=Healthy appearance, tops unbroken

5=25% of tops broken

9=majority of tops broken

Plant Appearance (PLTAR): This is a visual rating based on general plant appearance taking into account all factors of intactness, pest, and disease pressure.

1=Complete plant with healthy appearance

5=plants look OK

9=Plants not acceptable

ECB2R—European Corn borer 2nd Generation visual rating on a scale of 1-9; a 1 rating is showing no damage.

ECB1R—European Corn borer first generation leaf damage rated on a scale of 1-9; a 1 rating is showing no damage.

Ear Appearance Rating (EARAR): Ear size and uniformity rating

Good

5. Average

9. Poor

Crown Rot/Stalk Rot Rating (CRDSR) "Kick Test"

Kick base of 10 plants in a row at a point slightly above soil level.

No broken plants; stalk and brace roots intact 1 or 2 broken plants out of 10

3 broken plants out of 10

4 broken plants out of 10

5 broken plants out of 10

6 broken plants out of 10

7 broken plants out of 10

8 or 9 broken plants out of 10 all plants broken and/or brace roots severely deteriorated

Green Snap (GRSNP): The number of plants in yield rows that snapped below the ear due to brittleness associated with high winds are counted. For plots, count snapped plants out of 50 from two locations in each hybrid strip, sum, and the percentage is recorded.

Stay-green (STGRP): This is an assessment of the ability of a grain hybrid to retain green color as maturity approaches (taken near the time of black-layer) and should not be a reflection of hybrid maturity or leaf disease. Percentage of green tissue is recorded.

Stay Green Rating (STGRR): This is an assessment of the ability of a grain hybrid to retain green color as maturity approached (taken near the time of black layer or if major differences are noted later). This rating should not be a reflection of the hybrid maturity or leaf disease.

1=solid Green Plant

9=no green tissue

Ear/Kernel Rots (KRDSR): If ear or kernel rots are present, ten consecutive ears in each plot are husked and the number that have evidence of ear or kernel rots is counted, multiplied by 10, and rounded up to the nearest rating as described below. Ratings between hybrids should differ by at least a factor of 3. The disease primarily responsible for the rot is identified and recorded.

1=No rots, 0% of the ears infected.

3=Up to 10% of the ears infected.

5=11 to 20% of the ears infected.

7=21 to 35% of the ears infected.

9=36% or more of the ears infected.

Grain Quality (GRQUR): Several ears are husked back after black layer stage and kernel cap integrity and relative amount of soft starch endosperm along the sides of kernels is observed.

1=smooth kernel caps and or 10% or less soft starch

3=slight kernel wrinkles and or 30% soft starch

7=moderate kernel wrinkles and or 70% soft starch

9=severe kernel wrinkled and or 90% or more soft starch

Preharvest Hybrid Characteristics

Ear Type Fixed, Semi-Fixed, Flex (Home location: Thin outside row, every other plant for half of row.)

EARFR:

1=Flex

5=Semi-flex

9=Fixed

Husk Cover:

HSKCR:

1=Long

5=Medium

9=Short

Kernel Depth:

KRLNR:

1=Deep

5=Medium

9=Short (shallow)

Shank Length:

SHLNR:

1=Short

5=Medium

9=Long

Cob Color (COBCR):

1=White

5=Pink

9=Dark Red

Tassel size includes a classification of average, large, marginal, small and very large.

Shed Duration: (HUPLN) Pollen Shed Duration in HU-4 uniform plants in each plot are marked just as pollen shed begins. The date of first pollen shed is noted and the date when pollen shed is complete for all 4 plants is noted and the duration time is converted to heat units.

% Means for the above traits are just the observed value from the line divided by the average of all the lines it was tested with (times 100).

Count: is the number of reps done for the shed & silk data.

Kernel Row Number: Enter average of 3 ears (KRRWN): The average number of kernel rows on 3 ears.

Cob diameter (COBDR): Cob diameter to be taken with template.
 1: small
 5: Medium
 9: Large Corn: Harvest Trait Codes Yield Lb/Plot (GWTPN)

Test Weight in Lb/Bu (TWHMN)

Moisture % (GMSTP)

80K/FeAcre=number of 80K bags yielded from a production acre

80k % SetAvg=the 80K/FeAcre for the line/80K/FeAcre for the set it was tested in * 100.

Yield Stability=rating of yield stability across locations–how much it varies compared to the set average across locations.

COGP=Cost of Goods Production=cost per acre of producing this line.

| Form # | ABR. | Description | Input Value |
|---|---|---|---|
| A1 | EMRGN | Final number of pants per plot | # |
| A2 | REGNN | Region Developed: 1.Northwest 2.Northcentral 3.Northeast 4.Southeast 5.Southcentral 6.Southwest 7.Other | # |
| A3 | CRTYN | Cross type: 1.sc 2.dc 3.3w 4.msc 5.m3w 6.inbred 7.rel. line 8.other | |
| A4 | KRTPN | Kernel type: 1.sweet 2.dent 3.flint 4.flour 5.pop 6.ornamental 7.pipecorn 8.other | # |
| A5 | EMERN | Days to Emergence EMERN | #Days |
| B1 | ERTLP | % Root lodging: (before anthesis): | #% |
| B2 | GRSNP | % Brittle snapping: (before anthesis): | #% |
| C1 | TBANN | Tassel branch angle of 2nd primary lateral branch (at anthesis): | degree |
| C10 | HUPSN | Heat units to 50% pollen shed: (from emergence) | #HU |
| C11 | SLKCN | Silk color: | #/Munsell value |
| C12 | HU5SN | Heat units to 50% silk: (from emergence) | #HU |
| C13 | DSAZN | Days to 50% silk in adapted zone: | #Days |
| C14 | HU9PN | Heat units to 90% pollen shed: (from emergence) | #HU |
| C15 | HU19N | Heat units from 10% to 90% pollen shed: | #HU |
| C16 | DA19N | Days from 10% to 90% pollen shed: | #Days |
| C2 | LSPUR | Leaf sheath pubescence of second leaf above the ear (at anthesis) 1-9 (1 = none): | # |
| C3 | ANGBN | Angle between stalk and 2nd leaf above the ear (at anthesis): | degree |
| C4 | CR2LN | Color of 2nd leaf above the ear (at anthesis): value | #/Munsell |
| C5 | GLCRN | Glume Color: | #/Munsell value |
| C6 | GLCBN | Glume color bars perpendicular to their veins (glume bands): 1.absent 2.present | # |
| C7 | ANTCN | Anther color: | #/Munsell value |
| C8 | PLQUR | Pollen Shed: 1-9 (0 = male sterile) | # |
| C9 | HU1PN | Heat units to 10% pollen shed: (from emergence) | #HU |
| D1 | LAERN | Number of leaves above the top ear node: | # |
| D10 | LTBRN | Number of lateral tassel branches that originate from the central spike: | # |
| D11 | EARPN | Number of ears per stalk: | # |
| D12 | APBRR | Anthocyanin pigment of brace roots: 1.absent 2.faint 3.moderate 4.dark | # |
| D13 | TILLN | Number of tillers: | |
| D14 | HSKCN | Husk color 25 days after 50% silk: (fresh) | #/Munsell value |
| D2 | MLWVR | Leaf marginal waves: 1-9 (1 = none) | # |
| D3 | LFLCR | Leaf longitudinal creases: 1-9 (1 = none) | # |
| D4 | ERLLN | Length of ear leaf at the top ear node: | # cm |
| D5 | ERLWN | Width of ear leaf at the top ear node at the widest point: | # cm |
| D6 | PLHTN | Plant height to tassel tip: | # cm |
| D7 | ERHCN | Plant height to the top ear node: | # cm |
| D8 | LTEIN | Length of the internode between the ear node and the node above: | # cm |
| D9 | LTASN | Length of the tassel from top leaf collar to tassel tip: | # cm |
| E1 | HSKDN | Husk color 65 days after 50% silk: (dry) | #/Munsell value |
| E10 | DSGMN | Days from 50% silk to 25% grain moisture in adapted zone: | # Days |
| E11 | SHLNN | Shank length: | # cm |
| E12 | ERLNN | Ear length: | # cm |
| E13 | ERDIN | Diameter of the ear at the midpoint: | # mm |
| E14 | EWGTN | Weight of a husked ear: | # gm |
| E15 | KRRWR | Kernel rows: 1.indistinct 2.distinct | # |
| E16 | KRNAR | Kernel row alignment: 1.straight 2.slightly curved 3.curved | # |
| E17 | ETAPR | Ear taper: 1.slight 2.average 3.extreme | # |
| E18 | KRRWN | Number of kernel rows: | # |
| E19 | COBCN | Cob color: | #/Munsell value |
| E2 | HSKTR | Husk tightness 65 days after 50% silk: 1-9 (1 = loose) | # |
| E20 | COBDN | Diameter of the cob at the midpoint: | # mm |
| E21 | YBUAN | Yield: | # kg/ha |
| E22 | KRTEN | Endosperm type: 1.sweet 2.extra sweet 3.normal 4.high amylose 5.waxy 6.high protein 7.high lysine 8.super sweet 9.high oil 10.other | 3 |
| E23 | KRCLN | Hard endosperm color: | # /Munsell value |
| E24 | ALECN | Aleurone color: | # /Munsell value |
| E25 | ALCPR | Aleurone color pattern: 1.homozygous 2.segregating | # |
| E26 | KRLNN | Kernel length: | # mm |
| E27 | KRWDN | Kernel width: | # mm |
| E28 | KRDPN | Kernel thickness: | # mm |
| E29 | K1KHN | 100 kernel weight: | # gm |
| E3 | HSKCR | Husk extension: 1.short (ear exposed) 2.medium (8 cm) 3.long (8-10 cm) 4.very long (>10 cm) | # |
| E30 | KRPRN | % round kernels on 13/64 slotted screen: | #% |
| E4 | HEPSR | Position of ear 65 days after 50% silk: 1.upright 2.horizontal 3.pendent | # |
| E5 | STGRP | Staygreen 65 days after anthesis: 1-9 (1 = worst) | # |
| E6 | DPOPP | % dropped ears 65 days after anthesis: | # |
| E7 | LRTRP | % root lodging 65 days after anthesis: | % |
| E8 | HU25N | Heat units to 25% grain moisture: (from emergence) | # HU |
| E9 | HUSGN | Heat units from 50% silk to 25% grain moisture in adapted zone: | # HU |

Color Choices:
1.light green
2.medium green
3.dark green
4.very dark green
5.green-yellow
6.pale yellow
7.yellow
8.yellow-orange
9.salmon
10.pink-orange
11.pink
12.light red
13.cherry red
14.red
15.red and white
16.pale purple
17.purple
18.colorless
19.white
20.white capped
21.buff
22.tan
23.brown
24.bronze
25.variegated (describe)
26.other (describe)

DETAILED DESCRIPTION OF THE INVENTION

G07-NPFA7278 is shown in comparison with NP2467.

The inbred provides uniformity and stability within the limits of environmental influence for traits as described in the Variety Description Information (Table 1) that follows.

The inbred has been produced through a dihaploid system or is self-pollinated for a sufficient number of generations to give inbred uniformity. During plant selection in each generation, the uniformity of plant type was selected to ensure homozygosity and phenotypic stability. The line has been increased in isolated farmland environments with data on uniformity and agronomic traits being observed to assure uniformity and stability. No variant traits have been observed or are expected in G07-NPFA7278.

The best method of producing the invention is by planting the seed of G07-NPFA7278 which is substantially homozygous and self-pollinating or sib pollinating the resultant plant in an isolated environment, and harvesting the resultant seed.

TABLE 1

G07-NPFA7278
VARIETY DESCRIPTION INFORMATION

| #1 | Type: Dent |
| --- | --- |
| #2 | Region Best Adapted: Broadly adapted |

| | MG Group | Maturity Range | Hybrid RM (estimate) |
| --- | --- | --- | --- |
| | 7 | 113-117 | 113 |

| #3 | Plant Traits | |
| --- | --- | --- |
| | Plant Height | 69 in. |
| | Ear Height | 27 in. |
| | Anther Color | Pink |
| #4 | Ear and Kernel Traits | |
| | Cob Color | Red |
| | Kernel Color | Yellow |
| | Glume Color | Green w/red |
| | Silk Color | Green |
| #6 | Disease Resistance In Inbred * | |
| | Eyespot—Moderately susceptible | |
| | Goss Wilt—Highly resistant | |
| | Gray Leaf Spot—Moderately resistant | |

The data provided above is often a color. The Munsell code is a reference book of color, which is known and used in the industry and by persons with ordinary skill in the art of plant breeding. The purity and homozygosity of inbred G07-NPFA7278 is constantly being tracked using isozyme genotypes.

Isozyme Genotypes for G07-NPFA7278

Isozyme data were generated for inbred corn line G07-NPFA7278 according to procedures known and published in the art. The data in Table 2 gives the electrophoresis data on G07-NPFA7278.

TABLE 2

ELECTROPHORESIS RESULTS FOR G07-NPFA7278

| Inbred | ACP1_T | ACP4_T | ADH1T | IDH1T | IDH2T |
| --- | --- | --- | --- | --- | --- |
| G07-NPFA7278 | 2(3-4) | 2(2-4) | 4 | 4 | 4 |

| Inbred | MDH1T | MDH2T | MDH3T | MDH4T | MDH5T |
| --- | --- | --- | --- | --- | --- |
| G07-NPFA 7278 | 6 | 3 | 16 | 12 | 12 |

| Inbred | MDH6T | PGD1T | PGD2T | PGM1T | PGM2T | PHI1_T |
| --- | --- | --- | --- | --- | --- | --- |
| G07-NPFA7278 | Mm | 3.8 (2-3.8) | 5 | 9 | 3(3-4) | 4 |

Table 3 shows a comparison between G07-NPFA7278 and a comparable inbred NP2467.

G07-NPFA7278 has differs from NP2467 in cob color; the present invention has a red cob. The present invention has pink anther colors and the compared inbred has yellow anthers. The present invention does have a good female rating and the compared inbred only rates acceptable. The present inbred of this invention is medium height with low ears compared with the tall plant height and medium ear height of the compared inbred. These inbreds show differences across all Heat unit measurements with the present invention beginning and completing 50% silking and pollen shedding earlier than the compared inbred. The inbreds differ for Eyespot disease rating with the present invention having a less positive rating.

TABLE 3

PAIRED INBRED COMPARISON DATA

| NPCode | Type | Sterility | AntherColor | GlumeColor | CobColor |
| --- | --- | --- | --- | --- | --- |
| G07-NPFA7278 | Dent | No | Pink | Green w/red | Red |
| NP2467 | Dent | No | Yellow | Green | White |

| NPCode | KernelColor | Plant Height | plt hgt adjective | Ear Height |
| --- | --- | --- | --- | --- |
| G07-NPFA7278 | Yellow | 69 | (Medium) | 27 |
| NP2467 | Yellow | 73 | (Tall) | 31 |

| NPCode | ear hgt adjective | count | 50POL | 50SLK | Silk Delay | # Locs |
| --- | --- | --- | --- | --- | --- | --- |
| G07-NPFA7278 | (Low) | 33.0 | 1379.5 | 1416.5 | −37.0 | 13.0 |
| NP2467 | (Medium) | 37.0 | 1521.8 | 1538.0 | −16.2 | |

| NPCode | (1,000/acre) Final stand | 21-23 % Lrg Rnd | 21-23 % Lrg flat | 17-20 % Med Rnd |
| --- | --- | --- | --- | --- |
| G07-NPFA7278 | 32.5 | 14.7 | 20.0 | 22.9 |
| NP2467 | | | | |

| NPCode | 17-20 % Med Flat | 15-16 % Sm Rnd | 15-16 % Sm Flat | >24 < 15 % Discard | Overall Seeds/# |
| --- | --- | --- | --- | --- | --- |
| G07-NPFA7278 | 39.5 | 0.8 | 2.0 | 2.0 | 1601.0 |
| NP2467 | | | | | |

| NPCode | 80K/FEacre | 80k/% set avg | Yld Stabili | Female Rating |
| --- | --- | --- | --- | --- |
| G07-NPFA7278 | 97.5 | 114.7 | Average | Good |
| NP2467 | 73 | 86 | Average | Acceptable |

| NPCode | Carbonum Leaf Spot | Common Rust | Eyespot | Fusarium Cold | Goss Wilt |
| --- | --- | --- | --- | --- | --- |
| G07-NPFA7278 | | | MS | | HR |
| NP2467 | MR | MR | HR | MR | HR |

| NPCode | Gray Leaf Spot | NCLB | SCLB |
| --- | --- | --- | --- |
| G07-NPFA7278 | MR | | |
| NP2467 | MR | MR | HR |

*MS—moderately susceptible
*MR—moderately resistant
*HR—highly resistant

Table 4 shows the GCA (general combining ability) estimates of G07-NPFA7278 compared with the GCA estimates of the other inbreds. The estimates show the general combining ability is weighted by the number of experiment/location combinations in which the specific hybrid combination occurs. The interpretation of the data for all traits is that a positive comparison is a practical advantage. A negative comparison is a practical disadvantage. The general combining ability of an inbred is clearly evidenced by the results of the general combining ability estimates. This data compares the inbred parent in a number of hybrid combinations to a group of "checks". The check data is from our company's and other companies' hybrids which are commercial products and pre-commercial hybrids, which were grown in the same sets and locations.

TABLE 4

| Ent | NO4 | NO5 | NO6 | N | Yeild | Moist | Test_Wt | EarlyLdg | StalkLdg |
|---|---|---|---|---|---|---|---|---|---|
| HYBRID 4 | | | 14 | 14 | −29.3 | 2.1 | −0.4 | 3.1 | −1.9 |
| HYBRID 5 | | | 15 | 15 | −9.9 | 1.8 | −0.5 | 6.7 | 2.3 |
| HYBRID 6 | | | 14 | 14 | −21.5 | 1.8 | 0.0 | 6.7 | −0.9 |
| HYBRID 7 | | | 16 | 16 | −2.8 | 0.8 | −0.1 | 9.4 | −1.1 |
| HYBRID 8 | | | 15 | 15 | −37.6 | 0.6 | −0.4 | | −0.6 |
| HYBRID 9 | | | 16 | 16 | −20.6 | 2.0 | −0.3 | 0.0 | 2.8 |
| HYBRID 10 | | | 16 | 16 | −22.8 | 1.1 | 0.3 | 0.0 | −7.2 |
| HYBRID 11 | | | 13 | 13 | −10.4 | 0.5 | 0.3 | 1.1 | −0.1 |
| HYBRID 12 | | | 15 | 15 | −20.7 | −0.8 | 0.2 | 0.0 | 0.7 |
| HYBRID 13 | | | 27 | 27 | −14.5 | 1.4 | −0.7 | 2.7 | −1.5 |
| HYBRID 14 | | | 15 | 15 | −2.5 | 0.0 | −0.2 | 0.0 | 2.9 |
| HYBRID 15 | | | 13 | 13 | −7.5 | 1.4 | −0.4 | 3.1 | 1.9 |
| HYBRID 16 | | | 14 | 14 | −28.4 | 2.3 | −0.2 | 9.8 | −1.8 |
| HYBRID 17 | | | 16 | 16 | −13.1 | 2.0 | −0.8 | 1.1 | 0.7 |
| HYBRID 18 | | | 16 | 13 | −12.2 | 2.2 | 0.5 | 1.1 | −1.4 |
| HYBRID 19 | | | 13 | 13 | −12.3 | 3.4 | −1.2 | 1.1 | −3.1 |
| HYBRID 20 | | | 13 | 13 | −8.1 | 3.1 | −0.7 | 1.1 | −3.2 |
| HYBRID 21 | | | 13 | 13 | −12.7 | 2.8 | −0.7 | 1.1 | −7.0 |
| HYBRID 22 | | | 13 | 13 | 10.0 | 1.8 | 0.0 | −1.9 | 0.5 |
| G07-NPFA7278 HYBRID | | 38 | 122 | 160 | 8.2 | −1.3 | 0.3 | 4.1 | 1.6 |
| HYBRID 23 | 26 | 40 | 42 | 108 | 5.8 | 0.0 | −0.9 | 5.1 | −0.6 |
| HYBRID 24 | | | 13 | 13 | −3.4 | 0.7 | 0.1 | | 6.5 |
| HYBRID 25 | | | 12 | 12 | −12.9 | 0.0 | 0.4 | | −4.3 |
| HYBRID 26 | | | 15 | 15 | −22.1 | 2.3 | 0.6 | 0.0 | −17.3 |
| HYBRID 27 | | | 15 | 15 | −9.7 | 1.8 | −1.0 | 0.0 | −14.5 |
| HYBRID 28 | | | 16 | 16 | −12.3 | 0.4 | −0.2 | 0.0 | −4.0 |
| HYBRID 29 | | | 15 | 15 | −2.4 | 0.4 | 0.1 | | 3.2 |
| HYBRID 30 | | | 14 | 14 | −16.4 | 0.9 | 0.0 | 0.0 | −1.3 |
| XR = | | | 14 | 757 | −5.2 | 0.5 | −0.2 | 3.1 | −0.3 |
| XH = | | | 14 | 28 | −12.2 | 1.3 | −0.2 | 2.3 | −1.7 |
| XT = | | | 14 | 2 | 7.0 | −0.7 | −0.3 | 4.6 | 0.5 |

| Ent | Push | LateLdg | DrpEars | Emerge | Vigor | HUS50 | HUBL | PltHt | EarHt |
|---|---|---|---|---|---|---|---|---|---|
| HYBRID 4 | | 2.8 | 0.0 | | | | | −10.6 | 1.9 |
| HYBRID 5 | | 0.0 | −0.4 | | | | | −13.5 | −14.6 |
| HYBRID 6 | | 0.0 | 0.0 | | | | | −13.5 | −4.6 |
| HYBRID 7 | | 7.4 | −0.3 | | | | | | |
| HYBRID 8 | | 3.8 | 0.0 | | | | | | |
| HYBRID 9 | | 2.8 | 0.3 | | | | | | |
| HYBRID 10 | | 1.0 | 0.3 | | | | | | |
| HYBRID 11 | | −8.2 | 0.0 | | | | | −10.2 | −3.1 |
| HYBRID 12 | | 1.1 | 0.2 | | | | | | |
| HYBRID 13 | | 2.1 | 0.1 | | | | | | |
| HYBRID 14 | | 6.8 | −0.3 | | | | | | |
| HYBRID 15 | | −5.1 | 0.0 | | | | | −15.6 | −3.1 |
| HYBRID 16 | | 0.0 | 0.0 | | | | | −3.0 | −7.4 |
| HYBRID 17 | | 0.5 | −0.1 | | | | | | |
| HYBRID 18 | | 6.2 | 0.3 | | | | | | |
| HYBRID 19 | | −8.4 | 0.0 | | | | | −5.1 | −1.5 |
| HYBRID 20 | | −4.7 | 0.0 | | | | | 10.2 | −9.1 |
| HYBRID 21 | | −4.7 | 0.0 | | | | | 10.2 | −6.6 |
| HYBRID 22 | | −0.7 | 0.0 | | | | | −5.1 | 8.6 |
| G07-NPFA7278 HYBRID | 9.3 | −1.7 | 0.0 | −0.1 | 0.9 | 5.5 | −2473.6 | 4.0 | 7.0 |
| HYBRID 23 | −2.6 | 4.0 | 0.0 | −0.8 | 0.2 | −16.4 | −2586.3 | 0.5 | 2.2 |
| HYBRID 24 | | −7.0 | 0.0 | | | | | | |
| HYBRID 25 | | −7.7 | 0.0 | | | | | | |
| HYBRID 26 | | −3.8 | −1.3 | | | | | | |
| HYBRID 27 | | 5.2 | 0.3 | | | | | | |
| HYBRID 28 | | −7.1 | 0.3 | | | | | | |
| HYBRID 29 | | 4.5 | 0.0 | | | | | | |
| HYBRID 30 | | 6.8 | 0.0 | | | | | | |
| XR = | 1.1 | 0.3 | 0.0 | −0.4 | 0.6 | −4.7 | −2523.7 | 1.1 | 1.8 |
| XH = | 3.4 | −0.2 | 0.0 | −0.5 | 0.6 | −5.4 | −2529.9 | −4.3 | −3.0 |
| XT = | 3.4 | 1.2 | 0.0 | −0.5 | 0.6 | −5.4 | −2529.9 | 2.2 | 4.6 |

XR = GCA Estimate: Weighted by Expt
XH = GCA Estimate: Weighted by Parent2
Same as XH but using only those parent2 with two years data Table 5 A shows the inbred G07-NPFA7278 in hybrid combination is in comparison with another hybrid, which is adapted for the same region of the Corn Belt. When in this hybrid combination, the G07-NPFA7278 hybrid carries significantly more moisture, and significantly more test weight at harvest in comparison to the other commercial hybrid. The push test results for the present invention and for the commercial hybrid are similar. The present invention has a 38.3 and the $2^{nd}$ hybrid has a 37.1. The two hybrids show similar agronomic traits when grown together in this environment. However, the present invention does show a significantly different rating for stand and harvest population than does the commercial hybrid.

In contrast in the strip trials of Table 5B the hybrid of the present invention is yielding significantly different and does not have differently different moisture but is still carrying more test weight than is the comparison hybrid 2.

TABLE 5A

PAIRED HYBRID COMPARISON DATA

| Year | Hybrid | Yield | Moist | Test_Wt | EarlyRtLdg | StalkLdg | PushTest | LateRtLdg |
|---|---|---|---|---|---|---|---|---|
| Overall | G07-NPFA7278 | | | | | | | |
| | HYBRID 1 | 210.1 | 22.8 | 59.2 | 1.0 | 4.6 | 38.3 | 5.8 |
| | HYBRID 2 | 212.3 | 21.0 | 58.7 | 1.5 | 2.2 | 37.1 | 1.1 |
| | #Expts | 159.0 | 159.0 | 158.0 | 7.0 | 87.0 | 6.0 | 57.0 |
| | Diff | 1.8 | 1.8 | 0.5 | 0.4 | 2.5 | 3.3 | 4.6 |
| | Prob | 0.4 | 0.000*** | 0.000*** | 0.9 | 0.029** | 0.6 | 0.035** |

| Year | Hybrid | DrpEars | Stand | Stay-Green | GreenSnap | Harv_Pop | Emerge | Vigor |
|---|---|---|---|---|---|---|---|---|
| Overall | G07-NPFA7278 | | | | | | | |
| | HYBRID 1 | 0.0 | 59.2 | 42.3 | 2.7 | 29491.0 | 10.2 | 2.8 |
| | HYBRID 2 | 0.0 | 62.5 | 49.8 | 3.6 | 31205.0 | 10.1 | 2.9 |
| | #Expts | 19.0 | 172.0 | 20.0 | 13.0 | 170.0 | 32.0 | 33.0 |
| | Diff | 0.0 | 3.3 | 7.5 | 1.2 | 1744.0 | 0.1 | 0.2 |
| | Prob | 0.000*** | 0.1 | 0.5 | 0.000*** | 0.8 | 0.5 | |

| | Year | Hybrid | Intact | HUS50 | HUBL | PltHt | EarHt |
|---|---|---|---|---|---|---|---|
| | Overall | G07-NPFA7278 | | | | | |
| | | HYBRID 1 | 3.2 | 1329.0 | 2433.0 | 295.4 | 113.7 |
| | | HYBRID 2 | 1.9 | 1301.0 | 2453.0 | 289.5 | 112.5 |
| | | #Expts | 45.0 | 14.0 | 5.0 | 20.0 | 21.0 |
| | | Diff | 1.3 | 27.9 | 29.6 | 2.5 | 2.1 |
| | | Prob | 0.000*** | 0.008*** | 0.038** | 0.4 | 0.6 |

*.05 < Prob <= .10
**.01 < Prob <= .05
***.00 < Prob <= .01

TABLE 5B

PAIRED HYBRID COMPARISON STRIP DATA
NPFA7278

| Year | Hybrid | Yield | Moist | TestWT | Harvest Pop. | Vigor | Pct Barren |
|---|---|---|---|---|---|---|---|
| Overall | G07-NPFA7278 | | | | | | |
| | HYBRID 1 | 181.1 | 18.5 | 57.4 | 25330.0 | 4.2 | 3.0 |
| | HYBRID 3 | 193.8 | 18.6 | 56.8 | 27789.0 | 2.8 | 2.1 |
| | #Expts | 111.0 | 111.0 | 92.0 | 59.0 | 16.0 | 3.0 |
| | Diff | 12.7 | 0.0 | 0.7 | 2396.0 | 1.4 | 1.6 |
| | Prob | 0.000*** | 0.8 | 0.000*** | 0.000*** | 0.000*** | 0.3 |

| | Year | Hybrid | Pct GreenSnap | PctRL | PctSL | PctPush | PctDE | GLS |
|---|---|---|---|---|---|---|---|---|
| | Overall | G07-NPFA7278 | | | | | | |
| | | HYBRID 1 | 0.1 | 7.9 | 3.8 | 10.3 | 0.1 | 3.3 |
| | | HYBRID 3 | 0.1 | 21.1 | 3.6 | 12.4 | 0.1 | 4.7 |
| | | #Expts | 17.0 | 29.0 | 22.0 | 9.0 | 18.0 | 16.0 |
| | | Diff | 1.6 | 12.1 | 0.1 | 1.2 | 0.0 | 1.4 |
| | | Prob | 0.3 | 0.006*** | 0.9 | 0.8 | 1.0 | 0.034** |

*.05 < Prob <= .10
**.01 < Prob <= .05
***.00 < Prob <= .01

Table 6A shows the yield response of G07-NPFA7278 in hybrid combination in comparison with the plants in the environment around it at the same location. The data for the present inbred is showing consistently high yield results in comparison to the environment level. G07-NPFA7278 in hybrid combination is also showing similar yields as the comparison hybrid.

Table 6B shows the strip trial data from the same two hybrids. In the strip trials the present invention and the compared hybrid each are underachieving relative to the environment.

TABLE 6A

YIELD RESPONSE
Research Plots

| Research Plots Hybrid | Error | # Plots | \multicolumn{6}{c}{Environment Yield} |
|---|---|---|---|---|---|---|---|---|
| | | | 75 | 100 | 125 | 150 | 175 | 200 |
| HYBRID 2 | 20.2 | 168 | 99 | 122 | 145 | 168 | 191 | 215 |
| G07-NPFA7278 HYBRID | 22.2 | 172 | 97 | 120 | 143 | 165 | 188 | 211 |

TABLE 6B

YIELD RESPONSE
Strip Tests

| Strip Tests Hybrid | Error | # Strips | \multicolumn{6}{c}{Environment Yield} |
|---|---|---|---|---|---|---|---|---|
| | | | 75 | 100 | 125 | 150 | 175 | 200 |
| HYBRID 2 | 9.9 | 254 | 82 | 105 | 128 | 151 | 174 | 197 |
| G07-NPFA7278 HYBRID 1 | 10.6 | 237 | 73 | 98 | 122 | 147 | 172 | 197 |

TABLE 7

DISEASE RESISTANCE IN G07-NPFA7278 HYBRID

| Research_Name | GLSRating | NLSRating | SLBRating | NLBRating | GWRating |
|---|---|---|---|---|---|
| HYBRID 2 | 3 | | 4 | 3 | 2 |
| G07-NPFA7278 | | | | | |
| HYBRID 1 | 3 | | 4 | 1 | 1 |
| HYBRID 3 | 4 | | 4 | 1 | |

This invention also is directed to methods for producing a corn plant by crossing a first parent corn plant with a second parent corn plant wherein the first or second parent corn plant is an inbred corn plant from the line G07-NPFA7278. Further, both first and second parent corn plants can come from the inbred corn line G07-NPFA7278 which produces a self of the inbred invention. The present invention can be employed in a variety of breeding methods which can be selected depending on the mode of reproduction, the trait, and the condition of the germplasm. Thus, any breeding methods using the inbred corn line G07-NPFA7278 are part of this invention: selfing, backcrosses, hybrid production, and crosses to populations, and haploid by such old and known methods of using KWS inducers lines, Kransdor inducers, stock six material that induces haploids and anther culturing and the like.

All plants and plant cells produced using inbred corn line G07-NPFA7278 are within the scope of this invention. The invention encompasses the inbred corn line used in crosses with other, different, corn inbreds to produce (F1) corn hybrid seeds and hybrid plants and the grain produced on the hybrid plant. This invention includes plant and plant cells, which upon growth and differentiation produce corn plants having the physiological and morphological characteristics of the inbred line G07-NPFA7278.

Additionally, this maize can, within the scope of the invention, contain: a mutant gene such as, but not limited to, amylose, amylase, sugary 1, shrunken 1, waxy, AE (amylose extender), dull or imazethapyr tolerant (IT or IR™); or transgenic genes such as but not limited to insect resistant genes such as Corn Rootworm gene, Bacillus thuringiensis (Cry genes), or herbicide resistant genes such as Pat gene or Bar gene, EPSP, or disease resistant genes such as the Mosaic virus resistant gene, etc., or trait altering genes such as flowering genes, oil modifying genes, senescence genes and the like. The methods and techniques for inserting, or producing and/or identifying a mutation or making or reshuffling a transgene and introgressing the trait or gene in into the present invention through breeding, transformation, mutating and the like are well known and understood by those of ordinary skill in the art.

A number of different inventions exist which are designed to avoid detasseling in maize hybrid production. Some examples are switchable male sterility, lethal genes in the pollen or anther, inducible male sterility, male sterility genes with chemical restorers, sterility genes linked with parent. U.S. Pat. No. 6,025,546, relates to the use of tapetum-specific promoters and the barnase gene. U.S. Pat. No. 6,627,799 relates to modifying stamen cells to provide male sterility. Therefore, one aspect of the current invention concerns the present invention comprising one or more gene(s) capable of restoring male fertility to male-sterile maize inbreds or hybrids.

Various techniques for breeding, moving or altering genetic material within or into the present invention (whether it is an inbred or in hybrid combination) are also known to those skilled in the art. These techniques to list only a few are anther culturing, haploid production, (stock six is a method that has been in use for thirty years and is well known to those with skill in the art), transformation, irradiation to produce mutations, chemical or biological mutation agents and a host of other methods are within the scope of the invention. All parts of the G07-NPFA7278 plant including its plant cells produced using the inbred corn line is within the scope of this invention. The term transgenic plant refers to plants having genetic sequences, which are introduced into the genome of a plant by a transformation method and the progeny thereof. Transformation methods are means for integrating new genetic coding sequences into the plant's genome by the incorporation of these sequences into a plant through man's assistance, but not by breeding practices. The transgene once introduced into plant material and integrated stably can be moved into other germplasm by standard breeding practices.

Though there are a large number of known methods to transform plants, certain types of plants are more amenable to transformation than are others. Transformation of dicots is usually achievable for example, tobacco is a readily transformable plant. Monocots can present some transformation challenges, however, the basic steps of transforming plants monocots have been known in the art for about 15 years. The most common method of maize transformation is referred to as gunning or microprojectile bombardment though other methods can be used. The process employs small gold-coated particles coated with DNA which are shot into the transformable material. Detailed techniques for gunning DNA into cells, tissue, callus, embryos, and the like are well known in the prior art. One example of steps that can be involved in monocot transformation are concisely outlined in U.S. Pat. No. 5,484,956 "Fertile Transgenic Zea mays Plants Comprising Heterologous DNA Encoding Bacillus Thuringiensis Endotoxin" issued Jan. 16, 1996 and also in U.S. Pat. No. 5,489,520 "Process of Producing Fertile Zea mays Plants and Progeny Comprising a Gene Encoding Phosphinothricin Acetyl Transferase" issued Feb. 6, 1996.

Plant cells such as maize can be transformed not only by the use of a gunning device but also by a number of different techniques. Some of these techniques include maize pollen transformation (See University of Toledo 1993 U.S. Pat. No. 5,177,010); Whiskers technology (See U.S. Pat. Nos. 5,464, 765 and 5,302,523); electroporation; PEG on Maize; Agrobacterium (See 1996 article on transformation of maize cells in *Nature Biotechnology*, Volume 14, June 1996) along with numerous other methods which may have slightly lower efficiency rates. Some of these methods require specific types of cells and other methods can be practiced on any number of cell types.

The use of pollen, cotyledons, zygotic embryos, meristems and ovum as the target issue can eliminate the need for extensive tissue culture work. Generally, cells derived from meristematic tissue are useful. The method of transformation of meristematic cells of cereal is taught in the PCT application WO96/04392. Any number of various cell lines, tissues, calli and plant parts can and have been transformed by those having knowledge in the art. Methods of preparing callus or protoplasts from various plants are well known in the art and specific methods are detailed in patents and references used by those skilled in the art. Cultures can be initiated from most of the above-identified tissue. The only true requirement of the transforming plant material is that it can ultimately be used to form a transformed plant.

The DNA used for transformation of these plants clearly may be circular, linear, and double or single stranded. Usually, the DNA is in the form of a plasmid. The plasmid usually contains regulatory and/or targeting sequences which assists the expression or targeting of the gene in the plant. The methods of forming plasmids for transformation are known in the art. Plasmid components can include such items as: leader sequences, transit polypeptides, promoters, terminators, genes, introns, marker genes, etc. The structures of the gene orientations can be sense, antisense, partial antisense, or partial sense; multiple gene copies can be used. The transgenic gene can come from various non-plant genes (such as; bacteria, yeast, animals, and viruses) along with being from plants.

The regulatory promoters employed can be constitutive such as CaMv35S (usually for dicots) and polyubiquitin for monocots or tissue specific promoters such as CAB promoters, MR7 described in U.S. Pat. No. 5,837,848, etc. The prior art promoters, includes but is not limited to, octopine synthase, nopaline synthase, CaMv19S, mannopine synthase. These regulatory sequences can be combined with introns, terminators, enhancers, leader sequences and the like in the material used for transformation.

The isolated DNA is then transformed into the plant. After the transformation of the plant material is complete, the next step is identifying the cells or material, which has been transformed. In some cases, a screenable marker is employed such as the beta-glucuronidase gene of the uidA locus of *E. coli*. Then, the transformed cells expressing the colored protein are selected. In many cases, a selectable marker identifies the transformed material. The putatively transformed material is exposed to a toxic agent at varying concentrations. The cells not transformed with the selectable marker, which provides resistance to this toxic agent, die. Cells or tissues containing the resistant selectable marker generally proliferate. It has been noted that although selectable markers protect the cells from some of the toxic affects of the herbicide or antibiotic, the cells may still be slightly affected by the toxic agent by having slower growth rates. If the transformed material was cell lines then these lines are regenerated into plants. The cells' lines are treated to induce tissue differentiation. Methods of regeneration of cellular maize material are well known in the art.

A deposit of at least 2500 seeds of this invention will be maintained by Syngenta Seed Inc. Access to this deposit will be available during the pendency of this application to the Commissioner of Patents and Trademarks and persons determined by the Commissioner to be entitled thereto upon request. All restrictions on availability to the public of such material will be removed upon issuance of a granted patent of this application by depositing at least 2500 seeds of this invention at the American Type Culture Collection (ATCC), at 10801 University Boulevard, Manassas, Va. 20110. The date of deposit was Aug. 7, 2009. The ATCC number of the deposit is PTA-10263. The seeds were tested on Aug. 24, 2009 and found to be viable. The deposit of at least 2500 seeds will be from inbred seed taken from the deposit maintained by Syngenta Seed Inc. The ATCC deposit will be maintained in that depository, which is a public depository, for a period of 30 years, or 5 years after the last request, or for the enforceable life of the patent, whichever is longer, and will be replaced if it becomes nonviable during that period.

Additional public information on patent variety protection may be available from the PVP Office, a division of the US Government.

Accordingly, the present invention has been described with some degree of particularity directed to the preferred embodiment of the present invention. It should be appreciated, though that the present invention is defined by the following claims construed in light of the prior art so that modifications or changes may be made to the preferred embodiment of the present invention without departing from the inventive concepts contained herein.

I claim:

1. A seed of the maize inbred line designated G07-NPFA7278, representative seed of said line having been deposited under ATCC Accession Number PTA-10263.

2. A maize plant or plant part produced by growing the seed of claim 1.

3. An F1 hybrid maize seed produced by crossing a plant of maize inbred line G07-NPFA7278 according to claim 2 with a different maize plant and harvesting the resultant F1 hybrid maize seed.

4. A maize plant or plant part produced by growing the F1 hybrid maize seed of claim 3.

5. An F1 hybrid maize seed comprising an inbred maize plant cell of inbred maize line G07-NPFA7278, representative seed of said line having been deposited under ATCC Accession Number PTA-10263.

6. A maize plant produced by growing the F1 hybrid maize seed of claim 5.

7. A cell of a maize plant produced by growing the F1 hybrid maize seed of claim 5.

8. A process of introducing a desired trait into maize inbred line G07-NPFA7278 comprising: (a) crossing G07-NPFA7278 plants grown from G07-NPFA7278 seed, representative seed of which has been deposited under ATCC Accession Number PTA-10263, with plants of another maize line that comprise a desired trait to produce F1 progeny plants, wherein the desired trait is selected from the group consisting of waxy starch, male sterility, herbicide resistance, insect resistance, bacterial disease resistance, fungal disease resistance, and viral disease resistance; (b) selecting F1 progeny plants that have the desired trait to produce selected F1 progeny plants; (c) crossing the selected progeny plants with the G07-NPFA7278 plants to produce backcross progeny plants; (d) selecting for backcross progeny plants that have the desired trait to produce selected backcross progeny plants; and (e) repeating steps (c) and (d) at least three or more times to produce backcross progeny plants that comprise the desired trait and all of the physiological and morphological characteristics of corn inbred line G07-NPFA7278 listed in Table 1 when grown in the same environmental conditions.

9. A plant produced by the process of claim 8.

10. A maize plant having all the physiological and morphological characteristics of inbred line G07-NPFA7278, wherein a sample of the seed of inbred line G07-NPFA7278 was deposited under ATCC Accession Number PTA-10263.

11. A process of producing maize seed, comprising crossing a first parent maize plant with a second parent maize plant, wherein one or both of the first or the second parent maize plants is the plant of claim 10, and harvesting the resultant seed.

12. The maize seed produced by the process of claim 11.

13. The maize seed of claim 12, wherein the maize seed is hybrid seed.

14. A hybrid maize plant, or its parts, produced by growing said hybrid seed of claim 13.

15. The maize plant of claim 2, further defined as having a genome comprising at least one transgene or a gene conversion conferred by a transgene.

16. The maize plant of claim 15, wherein the gene confers a trait selected from the group consisting of herbicide tolerance; insect tolerance; resistance to bacterial, fungal, nematode or viral disease; waxy starch; male sterility and restoration of male fertility, modified carbohydrate metabolism or modified fatty acid metabolism.

17. A method of producing a maize plant, the method comprising the steps of (a) growing a progeny plant produced by crossing the plant of claim 10 with a second maize plant; (b) crossing the progeny plant with itself or a different plant to produce a seed of a progeny plant of a subsequent generation; (c) growing a progeny plant of a subsequent generation from said seed and crossing the progeny plant of a subsequent generation with itself or a different plant; and (d) repeating steps (b) and (c) for an additional 0-5 generations to produce a maize plant.

18. A method for developing a maize plant in a maize plant breeding program, comprising applying plant breeding techniques to the maize plant of claim 10, or its parts, wherein application of said techniques results in development of a maize plant.

19. The method for developing a maize plant in a maize plant breeding program of claim 18, wherein the plant breeding techniques are selected from the group consisting of recurrent selection, backcrossing, pedigree breeding, restriction fragment length polymorphism enhanced selection, genetic marker enhanced selection, and transformation.

\* \* \* \* \*